United States Patent [19]  [11] 3,979,454
Perrey et al.  [45] Sept. 7, 1976

[54] PROCESS FOR THE PRODUCTION OF ALKYL SULPHONIC ACID HYDROXY ALKYL AMIDES

[75] Inventors: Hermann Perrey; Harry Welz; Ralf Lange; Hans Rudolph; Hans Jürgen Rosenkranz, all of Krefeld, Germany

[73] Assignee: Bayer Aktiengesellschaft, Leverkusen, Germany

[22] Filed: Mar. 17, 1975

[21] Appl. No.: 559,283

[30] Foreign Application Priority Data
Mar. 29, 1974 Germany............................ 2415330

[52] U.S. Cl............................................. 260/556 A
[51] Int. Cl.$^2$...................................... C07C 143/74
[58] Field of Search.............. 260/556 A, 260/566 A

[56] References Cited
UNITED STATES PATENTS

| | | | |
|---|---|---|---|
| 2,213,360 | 9/1940 | Calcott et al.................. | 260/556 A |
| 2,334,186 | 11/1943 | Fox................................. | 260/556 A |
| 3,119,830 | 1/1964 | Burt................................ | 260/556 A |
| 3,755,439 | 8/1973 | Kennedy........................ | 260/556 A |

OTHER PUBLICATIONS
Wagner et al., APC 377842, June 8, 1943.

Primary Examiner—Arthur P. Demers
Attorney, Agent, or Firm—Burgess, Dinklage & Sprung

[57] ABSTRACT

Improved process for the production of alkyl sulphonic acid hydroxy alkyl amides by reacting alkyl sulphonic acid chlorides and hydroxy alkyl amines in the presence of acid binding agents wherein aqueous alkali hydroxide solution is used as acid-binding agent, the three components are applied in a substantially stoichiometric ratio, and the reaction is carried out by adding the alkyl sulphonic acid chloride to the hydroxy alkyl amine and adding to the mixture thus obtained the aqueous alkali hydroxide solutions at such a rate that the pH-value of the reaction mixture does not exceed pH 10.

10 Claims, No Drawings

PROCESS FOR THE PRODUCTION OF ALKYL SULPHONIC ACID HYDROXY ALKYL AMIDES

This invention relates to an improved process for the production of alkyl sulphonic acid hydroxy alkyl amides by reacting alkyl sulphonic acid chlorides with hydroxy alkyl amines in the presence of acid-binding agents.

It has been found that high yields of alkyl sulphonic acid hydroxy alkyl amides can be readily obtained by reacting alkyl sulphonic acid chlorides with hydroxy alkyl amines in the presence of aqueous alkali hydroxide solutions as an acid binding agent, using the three components in a substantially stoichiometric ratio and carrying out the reaction by adding the alkyl sulphonic acid chloride to the hydroxy alkyl amine and adding to the mixture thus obtained the aqueous alkali hydroxide solutions at such a rate that the pH-value of the reaction mixture does not exceed 10.

The process according to the invention is generally carried out at temperatures in the range from about −10° to about +50°C, preferably at temperatures in the range from about 0° to about 30°C and more especially at temperatures in the range from 10° to 20°C.

Preferably are used in the process according to the invention alkyl sulphonic acid chlorides of the type as are obtained by the sulphochlorination of alkanes, chloroalkanes and cycloalkanes (cf. Asinger, Chemie and Technologie der Paraffin-Kohlen-wasserstoffe, 1956, Akademie-Verlag Berlin, pages 395 – 474). The sulphonic acid chlorides correspond to the general formula:

$$R^1 - SO_2 - Cl \qquad (I)$$

in which:

$R_1$ represents an alkyl, chloroalkyl or cycloalkyl radical.

The alkyl radicals are linear or branched $C_1$—$C_{30}$—, preferably $C_8$—$C_{20}$—alkyl radicals.

The chloroalkyl radicals are linear or branched $C_1$—$C_{30}$—, preferably $C_8$—$C_{20}$—alkyl radicals, which are substituted at least once by chlorine.

As cycloalkyl radicals are mentioned preferably $C_5$—$C_7$—cycloalkyl radicals which may be substituted by chlorine, alkyl or chloroalkyl. The total of carbon atoms in the cycloalkyl radical should not be higher than 30 and amounts preferably to 5 to 20 carbon atoms. Especially should be mentioned the cyclopentyl and cyclohexyl residue.

Preferably $R^1$ stands for linear $C_8$—$C_{20}$—alkyl or —chloro—alkyl radicals.

In the process according to the invention there are used preferably mixtures of such alkyl sulphonic acid chlorides, as are obtained in the sulphochlorination of aliphatic hydrocarbons especially linear $C_8$—$C_{20}$—paraffins. The chloroalkyl sulphonic acid chloride content of these mixtures depends on the conditions applied in the sulphochlorination. These sulphonic acid chloride mixtures are normally characterized by their content of sulphochloride chlorine and carbon-bound chlorine (chain chlorine).

The hydroxy alkyl amines used in the process according to the invention may be selected from any compounds which contain as substituent on an aliphatic or cycloaliphatic radical at least one hydroxy group and at least one primary or secondary amino group; the radical may be substituted also by an aromatic radical.

The process according to the invention is preferably carried out with hydroxy alkyl amines corresponding to the general formula:

$$HN\begin{matrix}R^2-OH\\ \\ R^3\end{matrix} \qquad (II)$$

in which:

$R^2$ represents a divalent, optionally substituted aliphatic or cycloaliphatic radical, and $R^3$ represents hydrogen, an optionally substituted alkyl, cycloalkyl, aralkyl or aryl radical or the radical —$R^2$—OH, where $R^2$ is as defined above.

For $R^2$ are mentioned as representatives of the optionally substituted aliphatic or cycloaliphatic radicals preferably $C_2$—$C_8$—alkylene radicals which may be substituted by hydroxy, and cyclohexylene radicals which are optionally substituted by hydroxy and/or lower alkyl groups.

For $R^3$ should be mentioned:

as alkyl radicals especially $C_1$—$C_{14}$—alkyl radicals and as cycloalkyl radicals especially the cyclopentyl and cyclohexyl radical; as aralkyl radicals preferably phenylalkyl radicals such as phenyl ethyl, phenyl propyl, phenyl isopropyl, phenyl butyl, phenyl isobutyl and phenyl tert.-butyl; as aryl radicals preferably phenyl radicals optionally substituted by halogen atoms such as chlorine and bromine.

Preferably $R_2$ represents an $C_2$—$C_6$—alkylene radical which is optionally substituted once or several times by hydroxy, especially the ethylene or the isopropylene radical; and $R^3$ represents hydrogen or an $C_2$—$C_6$—alkylene radical which is optionally substituted once or several times by hydroxy.

The following are examples of compounds corresponding to general formula (II): alkanol amines such as ethanol amine, N-methyl ethanol amine, N-dodecyl ethanol amine, N-cyclohexyl ethanol amine, N-phenyl ethanol amine, N-benzyl ethanol amine, 3-amino-1-propanol, 1-amino-2-propanol isopropanol amine, 2-amino-2-methyl-1-propanol, 1-amino-3-butanol and N-cyclohexyl isopropanol amine; dialkanol amines such as diethanol amine, diisopropanol amine and 2-amino-2-methyl-1,3-propane diol; polyhydroxy alkyl amines such as 2-amino-2-hydroxy methyl-1,3-propane diol, and polyaminoalkanol amines such as N-(2-aminoethyl)-ethanol amine and N-methyl-N-(3-aminopropyl)-ethanol amine.

Particularly preferred compounds of formula (II) are ethanol amine, isopropanol amine, diethanol amine, diisopropanol amine and mixtures thereof.

The process according to the invention may also be carried out both in the absence and in the presence of a solvent which is inert under the reaction conditions. Representatives of such solvents are e.g. dimethyl formamide, lower aliphatic cetones and aliphatic or aromatic hydrocarbons. Preferred solvents are the hydrocarbons corresponding to the alkyl sulphonic acid chlorides used as starting material. For example there can be applied as starting material the solution of alkyl and/or cycloalkane sulphonic acid chlorides in alkanes and/or cycloalkanes as is normally obtained during the sulphochlorination reaction of alkanes and/or cycloalkanes. These solutions contain from 10 to 80% by weight and preferably from 30 to 50% by weight of sulphochlorides.

Starting materials, the melting point of which is between 20° and 50°C may be reacted also in molten state.

The aqueous alkali hydroxide solutions are preferably aqueous solutions of hydroxides of sodium and potassium. It is preferred to use aqueous sodium hydroxide. The solutions generally contain from 5 to 60% by weight preferably from 25 to 50% by weight of alkali hydroxide.

The process according to the invention is generally carried out as follows:

The entire quantity of hydroxy alkyl amine is introduced in the reaction vessel. To this the sulphochloride or mixture or solution thereof is added at temperatures from −10° to +50°C, preferably from 0° to 30°C especially from 10° to 20°C. To the mixture such obtained there is added at temperatures from −10° to +50°C, preferably 0° to 30°C and especially 10° to 20°C the aqueous alkali hydroxide solution at such a rate, that the pH-value of the reaction mixture does not exceed 10, preferably 9.

The pH-value is generally determined by means of a glass electrode. In principle the pH-value may also be measured by other methods, however no tests have been conducted to check whether these methods lead to the same results. The figures stated for the process according to the invention were obtained by the use of standard commercial-grade glass electrodes and pH-meters based thereon.

For the process according to the invention it is essential that hydroxy alkyl amine, sulphochloride and aqueous alkali hydroxide solution are applied in a substantially stoichiometric ratio. There are used per mol of sulphochloride 0,8 – 1,2 mols preferably 0,9 to 1,1 mols of alkali hydroxide and 1 to 1,3 mols, preferably 1 to 1,2 mols of hydroxy alkyl amine. A large excess of alkali hydroxide must be avoided, since otherwise alkyl sulphonic acid hydroxy alkyl amides would be obtained containing large quantities of sulphonate. The use of a larger excess of hydroxy alkyl amines would not be harmful but also not advantageous and would be uneconomical.

The isolation of the alkyl sulphonic acid hydroxy alkyl amides can be performed by different methods. The methods depend on the properties of the amides to be isolated. For example, the hydroxy alkyl amides of the alkyl sulphonic acids may be isolated from the reaction mixture, by freeing the mixture from the water and the solvent used, if any, by distillation under normal pressure or under reduced pressure and, providing the hydroxy alkyl amide is liquid at the temperature applied, filtering off the alkali chloride formed in the usual way.

It can be of particular advantage in working up the reaction mixture, especially when solutions of the sulphochlorides in hydrocarbons have been used, to initially distil off only the water and small quantities of the organic solvent, subsequently to filter off the alkali chloride precipitated and only then to remove the organic solvent in a second distillation stage. This second distillation stage may be carried out under normal or reduced pressure. Removal of the hydrocarbons by distillation may even be carried out with particular advantage by steam distillation in the usual way under reduced pressure.

The alkali chloride formed may also be separated off by separating off the aqueous phase of the reaction mixture in which it is present, followed by washing with water. In general, however, this is not advisable because difficultly separable emulsions are frequently formed in this case.

The hydroxy alkyl amides may also be extracted from the reaction solution. To this end, the water is initially distilled off from the reaction mixture, the extractant, for example a lower aliphatic alcohol such as methanol, is subsequently added and thereafter the alkali chloride formed and the extracted hydrocarbon phase and separated off. The extractant is removed from the extract by distillation and the residual reaction product is treated with steam under reduced pressure in order to remove residues of hydrocarbons boiling at temperatures higher than the extractant. Although this method of working up is generally more complicated, it can be of advantage in individual cases.

The alkyl sulphonic acid hydroxy amides according to the process of the invention constitute oily to wax-like substances depending both upon the number of carbon atoms in the alkyl radical of the sulphonic acid and upon the hydroxy alkyl amine used. They are mostly soluble in organic solvents and soluble or dispersible in water. They are effective emulsifiers.

By means of the process according to the invention it is possible to produce alkyl sulphonic acid hydroxy alkyl amides in a purity not achieved before and this in a simple and economical manner.

The process according to the invention is surprising because it is known that there can occur numerous of side reactions upon reaction of alkyl sulphonic acid chlorides with hydroxy alkyl amines (cf. Houben-Weyl, Methoden der organischen Chemie, Vol. XI, pages 388, 402, 403 (1955)). Due to the presence of the reactive hydroxy group the formation of alkyl sulphonic acid amino esters and their products of hydrolysis was to be expected.

Furthermore, it was to be expected that the use of aqueous alkali hydroxide solutions would result in hydrolysis of the alkyl sulphonic acid chloride to form the sulphonate, with no sulphonamide at all being formed in certain cases (cf. U.S. Pat. No. 2,213,360). For this reason, the reaction has hitherto generally been carried out in the absence of water with at least a one-molar excess of the hydroxy alkyl amine or without any excess of the hydroxy alkyl amine in the presence of at least stoichiometric quantities of a tertiary amine which acts as an acid-binding agent (cf. U.S. Pat. No. 2,334,186).

EXAMPLE 1

7.38 kg (121 mols) of ethanol amine are introduced into a 150 liter capacity stirrer-equipped vessel. 100 kg (116 mols) of an approximately 30 % by weight solution of alkyl sulphochlorides, obtained by the sulphochlorination of linear $C_{12}$—$C_{18}$—paraffins, in the corresponding paraffins (sulphochloride chlorine content 4.1 % and chain chlorine chlorine content 0.35 %) are run in with stirring over a period of 5 hours at a temperature of 15° to 20°C which is maintained by cooling with cooling brine. 10.66 kg of commercial-grade 45 % by weight aqueous sodium hydroxide (120 mols of NaOH) are then added dropwise over a period of 5 hours at the same temperature in such a way that the pH-value of the water-containing reaction mixture (as measured with a glass electrode) does not exceed pH 9, followed by stirring for 2 hours. The reaction mixture is then concentrated in a water jet vacuum at a sump temperature of up to 100°C, and the sodium chloride formed is filtered off under suction. After heating under a reduced pressure of 10 to 15 Torr to a sump temperature of 160° to 170°C, steam is blown in at that temperature under a pressure of 15 atms and the paraffins are removed by steam distillation. 33 kg of a golden yellow product which is highly viscous at room temperature are left after distillation. The substance is readily dispersible in water and soluble in organic solvents, such as methanol, ethanol, benzene, toluene, petroleum ether, ligroin, acetone and ethyl acetate.

The pH-value of a 5 % aqueous emulsion amounts to 6.5 and is still the same after boiling for 2 hours. Accordingly, the product does not contain any amino ester.

The sulphonate sulphur content according to Epton amounts to 0.93 % of sulphur, giving 9.1 % of alkyl sulphonate, so that the alkyl sulphonic acid hydroxy amide content amounts to 90,9 %.

EXAMPLE 2

475 g (6.3 mols) of isopropanol amine are introduced into a 10 liter capacity stirrer-equipped vessel. 5 kg (corresponding to 6.3 mols of sulphochloride) of an approximately 30 % by weight solution of alkyl sulphochlorides, obtained by sulphochlorinating linear $C_{10}$—$C_{18}$— paraffins, in the corresponding paraffins (sulphochloride chlorine content 4.5 % and chain chlorine chlorine content 0.5 %) are then run in with stirring over a period of 5 hours at a temperature of 15° to 20°C which is maintained by cooling with cooling brine. 1265 g of a 20 % by weight aqueous sodium hydroxide (63 mols of NaOH) are then added dropwise over a period of 4 hours at the same temperature. The pH-value measured in the watercontaining reaction mixture with a glass electrode remains below 9. After stirring for 2 hours, the reaction mixture is concentrated in a water jet vacuum at a sump temperature of up to 100°C and the sodium chloride formed is subsequently filtered off under suction. After heating under a reduced pressure of 10 to 15 Torr to a sump temperature of 160°C to 170°C, steam is blown in at that temperature under a pressure of 15 atms and the paraffins removed by steam distillation. Distillation leaves 1740 g of a dark yellow, highly viscous product. The substance is readily dispersible in water and soluble in methanol, ethanol, benzene toluene and ethyl acetate.

The pH-value of a 5 % aqueous solution amounts to 6.4 and is still the same after boiling for 2 hours. Accordingly, the product does not contain any amino ester.

The sulphonate sulphur content according to Epton amounts to 0.87 % of sulphur, giving 8.6 % of alkyl sulphonate, so that the $C_{10}$—$C_{18}$—alkyl sulphonic acid isopropanol amide content amounts to 91.4 %.

EXAMPLE 3

610 g (5.8 mols) of diethanol amine are introduced into a 10 liter stirrer-equipped vessel. 5 kg (5.8 mols) of the sulphochloride used in Example 1 are run in with stirring over a period of 4 hours at a temperature of 10° to 25°C which is maintained by cooling with cooling brine. 520 g of 45 % by weight aqueous sodium hydroxide (5.8 mols of NaOH) are then slowly added over a period of 4 hours at the same temperature, so that the pH-value remains below 10. After concentration in a water jet vacuum at a sump temperature of up to 100°C, the sodium chloride formed is filtered off under suction. After heating under a reduced pressure of 15 to 20 Torr to a sump temperature of 160° to 170°C, steam is blown in at that temperature under a pressure of 15 atms and the paraffins are removed by steam distillation. Distillation leaves 1880 g of a dark yellow, highly viscous product. The substance is readily soluble in methanol, ethanol, benzene and toluene, and readily emulsifiable in water.

An aqueous sample does not turn acidic on boiling, so that the product does not contain any amino ester. The sulphonate sulphur content according to Epton amounts to 1.20 % of sulphur, giving a $C_{12}$—$C_{18}$—alkyl sulphonic acid diethanol amide content of 88.2 %.

EXAMPLE 4

770 g (5.8 mols) of diisopropanol amine are melted at 45°C, followed by the addition with stirring at that temperature of about 500 g of the alkyl sulphochloride solution used in Example 1. After cooling to approximately 20°C, further sulphochloride solution is added at that temperature until a total quantity of 5 kg (5.8 mols of sulphochloride) is reached. 520 g of 45 % by weight aqueous sodium hydroxide (5.8 mols of NaOH) are then added dropwise over a period of 5 hours at the same temperature, the pH-value in the reaction mixture being kept below 9, followed by stirring for another 2 hours. The reaction mixture is then concentrated in a water jet vacuum at a sump temperature of up to 100°C, and the sodium chloride formed filtered off under suction. After heating under a reduced pressure of 20 to 25 Torr to a sump temperature of 160° to 180°C, steam is blown in at that temperature under a pressure of 15 atms and the paraffins are removed by steam distillation. Distillation leaves 2060 g of a dark yellow highly viscous product. The pH-value of a 5 % aqueous emulsion amounts to 6.6 and is still the same after boiling for 2 hours. Accordingly, the product does not contain any amino ester.

The sulphonate sulphur content according to Epton amounts to 1.3 % of sulphur, giving 12.7 % of alkyl sulphonate so that the $C_{12}$—$C_{18}$—alkyl sulphonic acid diisopropanol amide content amounts to 87.3 %.

EXAMPLE 5

3.55 kg (58 mols) of ethanol amine and 4.35 kg (58 mols) isopropanol amine are introduced into a 150 liter stirrer-equipped vessel. 100 kg of the sulphochloride used in Example 1 (116 mols of sulphochloride) are run in with stirring and intensive external cooling at a temperature of 15° to 20°C. 10.66 kg of commercial-grade 45 % sodium hydroxide (120 mols of NaOH) are then slowly added over a period of 5 hours at the same temperature in such a way that the pH-value of the water-containing reaction medium remains below 9. After stirring for 2 hours, the reaction mixture is concentrated in a water jet vacuum at a sump temperature of up to 100°C. The sodium chloride precipitated is then filtered off under suction and the filtrate is freed from paraffin left in the reaction product by steam distillation under a pressure below 10 Torr and at a sump temperature in the range from about 160° to 170°C. To this end, the filtrate is first heated under the reduced pressure to the sump temperature indicated, after which steam is gently blown in under a pressure of 15 atms. 33.8 kg of a dark yellow product which is highly viscous at room temperature are obtained in this way.

The pH-value of a 5 % aqueous emulsion amounts to 6.5 and is still the same after boiling for 2 hours.

The sulphonate sulphur content according to Epton amounts to 1.3 % of sulphur, giving 12.7 % of alkyl sulphonate, so that the $C_{12}$—$C_{18}$—alkyl sulphonic acid hydroxy alkyl amide content amounts to 87.3 %.

EXAMPLE 6 (Comparison Example)

Stoichiometric quantities of the reaction components were used in a general method for the preparation of aryl sulphonic acid amides (cf. Houben-Weyl, Vol. IX, page 609 (1955) for comparison with the process according to the invention.

71 g (1.2 mols) of ethanol amine and 465 g of a 10 % by weight aqueous sodium hydroxide (1.2 mols of NaOH) are introduced into a 2 liter stirrer-equipped flask. The pH-value of the aqueous solution, measured with a glass electrode, amounts to 13.3. 1000 g of a 30 % by weight alkyl sulphochloride solution (1.2 mols) as used in Example 1 are added dropwise with stirring over a period of 4 hours at a reaction temperature between 15° and 20°C. The pH-value measured with the glass electrode in the reaction medium is above 10 for almost the entire reaction time. It only drops below pH 10 towards the end of the reaction.

The reaction mixture is then concentrated in a water jet vacuum under a pressure of 15 to 20 Torr at a sump temperature of up to 100°C, and the sodium chloride formed is filtered off under suction. After heating in a water jet vacuum under a pressure of 15 to 20 Torr to a sump temperature of 160° to 170°C, steam is blown in at that temperature under a pressure of 15 atms and the residual paraffins thus removed by steam distillation. Distillation leaves 330 g of a product which is highly viscous at room temperature.

The sulphonate sulphur content according to Epton amounts to 4.5 % of sulphur, giving a sulphonate content of 45.8 %. Accordingly, only 54.2 % of the product obtained consists of $C_{12}$—$C_{18}$—alkyl sulphonic acid ethanol amide.

We claim:
1. In the known process for the production of alkyl sulphonic acid hydroxy alkyl amides by reacting alkyl sulphonic acid chlorides and hydroxy alkyl amines in the presence of acid binding agents the improvement comprising using an aqueous alkali hydroxide solution as acid-binding agent, applying the three components in such a ratio, that 0.8 to 1.2 moles of alkali hydroxide and 1 to 1.3 moles of hydroxy alkyl amine are used per mole of sulphonic acid chloride, and carrying out the reaction by adding the alkyl sulphonic acid chloride to the hydroxy alkyl amine and adding to the mixture thus obtained the aqueous alkali hydroxide solution at such a rate that the pH-value of the reaction mixture does not exceed pH 10.

2. A process as claimed in claim 1, wherein alkyl sulphonic acid chlorides corresponding to the formula

in which
R¹ represents an alkyl chloroalkyl or cycloalkyl radical, are used.

3. A process as claimed in claim 1, wherein the hydroxy alkyl amines used correspond to the general formula

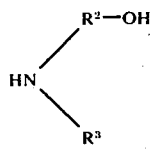

in which
R² represents a substituted or unsubstituted divalent aliphatic or cycloaliphatic radical, and
R³ represents hydrogen, a substituted or unsubstituted alkyl, cycloalkyl, aralkyl or aryl radical or the radical —R²—OH where R² is as defined above.

4. A process as claimed in claim 1, wherein the alkyl sulphonic acid chlorides used correspond to the formula

in which
R⁴ represents a linear or branched $C_8$—$C_{20}$—alkyl and/or chloroalkyl radical.

5. A process as claimed in claim 1, wherein ethanol amine, isopropanol amine, diethanol amine, diisopropanol amine or mixtures thereof are used as the hydroxy alkyl amine.

6. A process as claimed in claim 1, wherein the reaction is carried out at temperatures in the range of from −10° to 50°C.

7. A process as claimed in claim 1, wherein the reaction is carried out at temperatures in the range from 0° to 30°C.

8. A process as claimed in claim 1, wherein from 0.9 to 1.1 mols of alkali hydroxide are used per mol of sulphochloride.

9. A process as claimed in claim 1, wherein 1 to 1.2 mols of hydroxy alkyl amine are used per mol of sulphochloride.

10. A process according to claim 7 wherein the reaction is carried out at a temperature in the range from 10° to 20°C.

* * * * *